US012673189B2

(12) United States Patent　　　　(10) Patent No.:　US 12,673,189 B2
Rousu　　　　　　　　　　　　　　　(45) Date of Patent:　　　　Jul. 7, 2026

(54) INFLATABLE PERFUSION BALLOON WITH OUTER MESH AND RELATED METHODS

(71) Applicant: C.R. BARD, INC., Tempe, AZ (US)

(72) Inventor: Corey Rousu, Cave Creek, AZ (US)

(73) Assignee: C.R. BARD, INC., Tempe, AZ (US)

( * ) Notice: Subject to any disclaimer, the term of this patent is extended or adjusted under 35 U.S.C. 154(b) by 2240 days.

(21) Appl. No.: 15/560,660

(22) PCT Filed: Apr. 6, 2016

(86) PCT No.: PCT/US2016/026158
§ 371 (c)(1),
(2) Date: Sep. 22, 2017

(87) PCT Pub. No.: WO2016/164420

PCT Pub. Date: Oct. 13, 2016

(65) Prior Publication Data

US 2018/0099126 A1　　　Apr. 12, 2018

Related U.S. Application Data

(60) Provisional application No. 62/143,472, filed on Apr. 6, 2015.

(51) Int. Cl.
A61M 25/10　　　　　(2013.01)
(52) U.S. Cl.
CPC ........ A61M 25/1002 (2013.01); A61M 25/10 (2013.01); A61M 25/1029 (2013.01); A61M 2025/1004 (2013.01); A61M 2025/1031 (2013.01); A61M 25/104 (2013.01); A61M 2025/1072 (2013.01);

(Continued)

(58) Field of Classification Search
CPC .. A61M 2025/1097; A61M 2025/1072; A61M 2025/1084; A61M 2025/1004; A61M 2025/1031; A61M 25/10; A61M 25/1002; A61M 25/104
See application file for complete search history.

(56) References Cited

U.S. PATENT DOCUMENTS

| | | | | |
|---|---|---|---|---|
| 5,505,702 | A | * 4/1996 | Arney | A61M 25/104 |
| | | | | 604/101.01 |
| 5,556,382 | A | * 9/1996 | Adams | A61M 25/104 |
| | | | | 604/103.09 |
| 5,643,210 | A | 7/1997 | Iacob | |

(Continued)

FOREIGN PATENT DOCUMENTS

| | | |
|---|---|---|
| CN | 102143777 A | 8/2011 |
| CN | 103415316 A | 11/2013 |

(Continued)

*Primary Examiner* — Diane D Yabut
(74) *Attorney, Agent, or Firm* — Dickinson Wright PLLC; Andrew D. Dorisio; Nicholas P. Coleman

(57) ABSTRACT

An apparatus for performing a medical procedure in the vasculature comprises an inflatable perfusion balloon including a passage for transmitting fluid in an inflated condition of the balloon. A metal or wire mesh is positioned along or over at least a portion of the inflatable balloon. The mesh may allow fluid to flow through the wire mesh into the passage when the balloon is inflated. The mesh may comprise a wire sock or sleeve, and may comprise a shape memory material, such as Nitinol. Related methods are also disclosed.

12 Claims, 3 Drawing Sheets

(52) U.S. Cl.
CPC .............. *A61M 2025/1084* (2013.01); *A61M 2025/1097* (2013.01); *A61M 2205/0266* (2013.01)

(56) References Cited

U.S. PATENT DOCUMENTS

| | | | | | |
|---|---|---|---|---|---|
| 5,720,723 | A | * | 2/1998 | Adams ................ | A61M 25/104 604/103.01 |
| 5,810,767 | A | | 9/1998 | Klein | |
| 8,388,573 | B1 | * | 3/2013 | Cox .................. | A61M 25/1002 604/103.01 |
| 2011/0144742 | A1 | | 6/2011 | Madrid et al. | |
| 2012/0109179 | A1 | | 5/2012 | Murphy | |
| 2016/0136397 | A1 | * | 5/2016 | Konstantino ....... | A61M 25/104 604/103.02 |
| 2016/0175565 | A1 | * | 6/2016 | Schaffer ............ | A61M 25/1002 606/194 |

FOREIGN PATENT DOCUMENTS

| | | | |
|---|---|---|---|
| CN | 104363949 | A | 2/2015 |
| EP | 2241284 | A1 | 10/2010 |
| JP | H0751383 | A | 2/1995 |
| JP | H07507697 | A | 8/1995 |
| JP | 2002523192 | A | 7/2002 |
| WO | WO9317748 | A | 9/1993 |
| WO | WO0012169 | A1 | 3/2000 |
| WO | WO2012099979 | | 7/2012 |
| WO | WO2014176422 | | 10/2014 |

* cited by examiner

INFLATABLE PERFUSION BALLOON WITH OUTER MESH AND RELATED METHODS

This application claims the benefit of U.S. Provisional Patent Application Ser. No. 62/143,472, the disclosure of which is incorporated herein by this reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Expandable devices, such as balloons, are widely used in medical procedures. In the case of a balloon, it is inserted into the body, typically on the end of a catheter, until the balloon reaches the area of interest. Adding pressure to the balloon causes the balloon to inflate. In one variation of use, the balloon creates a space inside the body when the balloon inflates.

Balloons may be used in the heart valves, including during Balloon Aortic Valvuloplasty (BAV) and Transcatheter Aortic Valve Implantation (TAVI). The balloons can be used to open a stenosed aortic valve. A stenosed valve may have hard calcific lesions, which may require the use of a robust balloon to "crack" the lesions. Additionally, a precise inflated balloon diameter may be desired for increased control.

Balloons may be used to move plaque away from the center of a vascular lumen toward the vasculature walls, such as during an angioplasty or a peripheral vasculature procedure. During this procedure, a balloon tipped catheter is placed in a vascular obstruction. As the balloon is inflated, the vessel constriction is dilated, resulting in improved blood flow.

For the traditional approach, two basic types of balloons are utilized: One is a high pressure, low-compliance balloon. The other is a lower pressure, high-compliance balloon.

High-compliance medical balloons are often composed of urethane, latex, silicone, PVC, Pebax, and other elastomers. As the pressure in a high-compliant balloon is increased, the balloon dimensions expand. Once the pressure is reduced, the high-compliance medical balloon may return to its original shape, or near its original shape. High-compliance medical balloons can easily expand several times in volume between zero inflation pressure and burst.

Traditional high-compliance medical balloons can be inadequate for many reasons. High-compliance, or highly elastic medical balloons typically cannot reach high pressures because their walls have a low tensile strength and their walls thin out as the balloon expands. In some instances, high-compliance medical balloons provide insufficient force to complete a procedure. Exceeding the rated pressure of a high-compliance medical balloon creates an excessive risk of balloon failure which can lead to serious complications for the patient. Moreover, high-compliance medical balloons also have poor shape control. As a high-compliance medical balloon expands, it may assume a shape dictated mostly by the particulars of the environment inside the patient rather than the clinical goals. In some cases, this can be contrary to what the medical practitioner desires.

Many medical procedures, such as BAV and TAVI in particular, are predicated on forming a particular balloon shape reliably.

Low-compliance, high pressure medical balloons substantially retain their shape under comparatively high pressures. PET (polyethylene terephthalate) is the most common material for use in high pressure low-compliance balloons. PET is commonly used for high-performance angioplasty balloons. PET is stronger than other polymers, can be molded into a variety of shapes and can be made very thin (e.g., 5 μm to 50 μm (0.0002 in. to 0.002 in.)), thus giving these balloons a low profile. PET is very stiff so balloons made from PET may be difficult to pack or fold into a small diameter and may have poor trackability (i.e., the ability to slide and bend over a guidewire deployed through a tortuous vessel). Further, balloons made from PET, while stronger than most other balloons made from homogenous polymers, may still not be strong enough to hold pressures sufficient to complete certain medical procedures. Additionally, with a large balloon diameter (For example, 20 mm or greater), a PET balloon still has excessive compliance for procedures such as BAV and TAVI.

Nylon balloons are an alternative material for low-compliance, high pressure balloons. However, these nylon balloons are typically weaker than PET balloons and so can contain less pressure. Nylon readily absorbs water, which can have an adverse effect on Nylon's material properties in some circumstances. Nylon has improved puncture resistance over PET and is more flexible than PET.

Fiber-reinforced composite balloons are another alternative low-compliance, high pressure medical balloon. Such fiber-reinforced composite balloons can advantageously sustain high pressures, provided precise shape control, and are highly resistant to tear and puncture. The manufacturing process for fiber-reinforced balloons, however, can be complicated and expensive, requiring the application of multiple different layers of fibers in order to achieve the desired support. Often, at least one of these layers consists of a fabric de-convolution pattern layer wrapped around a base balloon. Such forming and wrapping of the fabric pattern layer can be cumbersome, labor and equipment intensive, and time consuming. Such a fabric may also require the formation of openings to accommodate fluid flow, which can lead to further manufacturing difficulties and may also weaken the fabric.

Thus, there exists the need to create a reinforced perfusion balloon that can be manufactured quickly and easily while still maintaining its ability to withstand high pressures, provide precise shape control, and allow for the desired perfusion to occur in an efficient and effective manner.

SUMMARY OF THE DISCLOSURE

In general, a perfusion balloon including an outer mesh is proposed. More specifically, an inflatable perfusion balloon includes a passage for allowing fluid flow in an inflated condition of the balloon. A mesh, such as a woven or non-woven wire structure, is positioned over or along at least a portion of the balloon allows fluid to flow through the mesh into the passage when the balloon is inflated. The technical effect of this approach is to create a reinforced perfusion balloon that can be manufactured quickly and easily while still maintaining its ability to withstand high pressures, provide precise shape control, and allow for the desired perfusion to occur in an efficient and effective manner.

According to the following aspects of the disclosure, the technical effects may be achieved by an apparatus for performing a medical procedure in the vasculature comprising an inflatable perfusion balloon including a passage for transmitting fluid in an inflated condition of the balloon, and a wire mesh positioned over at least a portion of the inflatable balloon. In one embodiment, the balloon comprises a first cell and a second cell in a single cross-section of the balloon. A space is provided between the first cell and the second cell, and openings in the wire mesh allow fluid to flow from external to the balloon, into the space, and to the passage. The passage may be surrounded by the first and second cells, and the wire mesh overlies the first and second cells of the balloon. The first and second cells may each include an inflation lumen, which may be formed by a proximal next at least partially covered by the wire mesh.

The wire mesh may comprise a metal and/or a shape-memory material, such as Nitinol, and may include one or more helical wires. The balloon may include tapered end regions and a central region, the wire mesh extending along at least the central region of the balloon. The wire mesh may comprise a reticulated structure including one or more openings in fluid communication with the passage when the balloon is inflated.

According to a further aspect of the disclosure, an apparatus for performing a medical procedure in the vasculature includes an inflatable perfusion device including a first balloon and a second balloon in a single cross-section of the device and a wire mesh positioned over at least a portion of the first and second balloons along the single cross-section of the device. The first and second balloons may comprise first and second cells of a single balloon, and the wire mesh may comprise a metal and/or a shape memory material.

Each balloon may comprise tapered end portions and a central portion, the wire mesh extending along at least the central portions of the balloons. The wire mesh may include openings in fluid communication with the passage when the device is inflated. Specifically, the wire mesh may include at least one opening positioned between the first and second balloons. Each balloon may also comprise a proximal neck for receiving a fluid for causing the balloon to inflate, and wherein the wire mesh at least partially covers the proximal necks.

A further aspect of the disclosure pertains to an apparatus for performing a medical procedure in the vasculature. The apparatus comprises an inflatable perfusion balloon, and a wire sock positioned over at least a portion of the balloon. In one embodiment, the wire sock comprises a metal mesh, and the balloon comprises tapered end portions and a central portion, the wire sock or metal mesh extending along at least the central portion of the balloon. The wire sock may have one or more openings in fluid communication with the passage when the device is inflated.

Still another aspect of the disclosure pertains to an apparatus for performing a medical procedure in the vasculature. The apparatus comprises an inflatable perfusion balloon including a passage for transmitting fluid in an inflated condition of the balloon. A sleeve comprising a shape memory material is positioned over at least a portion of the inflatable balloon. The sleeve may comprise a wire mesh and/or a shape memory material, such as Nitinol. The balloon may comprise plural cells in a single cross section.

Yet another aspect of the disclosure pertains to an apparatus for performing a medical procedure in the vasculature. The apparatus comprises an inflatable perfusion balloon including a passage for transmitting fluid when the balloon is inflated, and a compressive mesh positioned over at least a portion of the inflatable balloon.

Still a further aspect of the disclosure pertains to an apparatus for performing a medical procedure in the vasculature. The apparatus comprises an inflatable perfusion balloon including a passage for transmitting fluid when the balloon is inflated, and a metal mesh positioned over at least a portion of the inflatable balloon.

Yet another aspect of the disclosure pertains to a method of forming a perfusion balloon. As noted above, the method may comprise providing a wire mesh over the perfusion balloon. This can be done by winding a wire over an outer surface of the balloon, or inserting the perfusion balloon into a tube formed of the wire mesh. The method may also include attaching the wire mesh to the perfusion balloon. The wire mesh may also be used to provide a compressive force on the balloon.

DETAILED DESCRIPTION

The invention disclosed pertains to an inflatable device in the nature of a balloon and, in particular, a perfusion balloon. The novel features of the invention are set forth with particularity in the claims that follow. A better understanding of the features and advantages of the invention will be obtained by reference to the following detailed description that sets forth illustrative embodiments, in which the principles of the invention are utilized, and the accompanying drawings.

Figure 1:
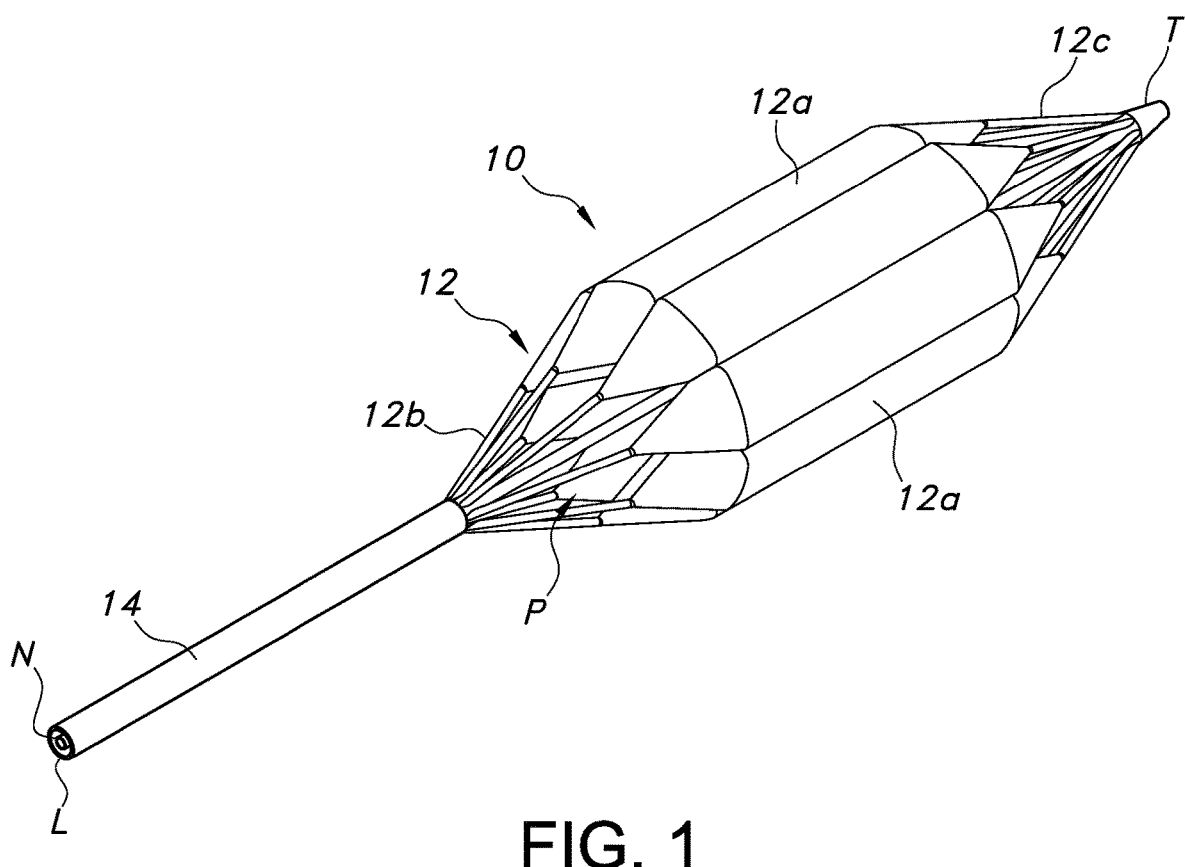
FIG. 1 is a perspective view of an inflatable device in the expanded condition.

FIG. 1 shows an inflatable device 10 including a balloon 12 supported by a catheter shaft 14. It can be understood that the balloon 12 of the device 10 may have multiple inflatable cells 12a in a single cross-section, which may be individual, separately inflatable balloons (each having a separate inflation lumen, as noted) or parts of a single balloon. The latter may be achieved by a segmented, elongated structure that is folded in a manner that causes the cells 12a to surround passage P extending along a central axis X, along which fluid such as blood may continue to flow, even when the balloon 12 is fully inflated (which may be done through a single inflation lumen, or each balloon could have its own inflation lumen). A full description of this type of balloon may be found in International Patent Application Publication No. WO2012099979A1. However, other forms of perfusion balloons could also be used, such as for example a tube-shaped balloon, one having a peripheral (e.g., helical) channel for purposes of allowing fluid flow to occur during inflation, an annular or tubular balloon, or any combination of these technologies.

The balloon 12 may be formed of any suitable material, including but not limited to urethane, latex, silicone, PVC, Pebax, and other elastomers, PET, Nylon, other polymers, and any combination of the foregoing. Examples of materials useful in making compliant (or elastic) balloons include various polymeric materials (including materials already known to be useful for making compliant medical balloons), e.g., elastomeric membranes having a high degree of linearity (non-plasticity) for a wide range of stress and strain values. Such materials include various Silicones, latex, Kraton, various thermoplastic elastomers (TPE's) particularly styrene-ethylene/butylene-styrene block copolymers (SEBS)-based TPE's (such as C-Flex), polysiloxane modified SEBS and their associated families, polyvinylchloride (PVC), crosslinked polyolefins such as polyethylene, and various polyurethanes. Examples of materials used in making noncompliant balloons (e.g., inelastic balloons) include many of the polyamides (e.g., the Nylons), thermoplastic polyamides, polyesters, polyphenylene sulfides, ultra-high molecular weight polyethylene, and PET.

In the illustrated embodiment using the multi-cellular balloon 12, each cell 12a includes a proximal neck 12b in communication with an inflation lumen L and a distal neck 12c. In any case, the device 10 may also include a guidewire lumen N extending along the central axis X, which may form part of a catheter tube 14 to which the balloon 12 may be attached (such as at a distal end thereof at the necks 12c, and in connection with a tip T).

In order to constrain the cells 12a in this configuration, a wire mesh 16 is provided along an outer surface thereof. The wire mesh 16 may be positioned atop the balloon 12 (over cells 12a in particular), and may be provided as a winding, as discussed below, or as an open-ended, flexible wire sock, tube, or sleeve for receiving the balloon 12 in the folded configuration. The wire mesh 16 may be arranged to form the balloon 12 in a particular shape, such as one having generally conical or tapering end portions C and a central barrel portion B. This barrel portion B is also sometimes referred to as the "working" portion of the balloon 12 because it is the structure that makes contact with the valve or other part of the vasculature being treated.

For purposes of this disclosure, the term "mesh" is intended to refer to a material having an open texture with spaced holes, and "wire" means the mesh comprises one or more filaments or a similar thin flexible members. In one particular embodiment, the wire mesh 16 is arranged such that the holes comprise a greater part of the area of the mesh than the solid material forming it. In other words, the mesh is more open than closed, and thus promotes the free flow of fluid while still provided a restraint for the underlying balloon 12.

The mesh 16 may be formed of a material capable of expanding with the balloon(s) during inflation, such as a metal (including one that is radiopaque) or a combination of metal and polymer or plastic materials. In one particular embodiment, the mesh 16 is made of a shape memory material or alloy, such as Nitinol. This type of material may be annealed such that it can maintain a particular shape based on temperature (such as a low profile at body temperature).

Figure 6:
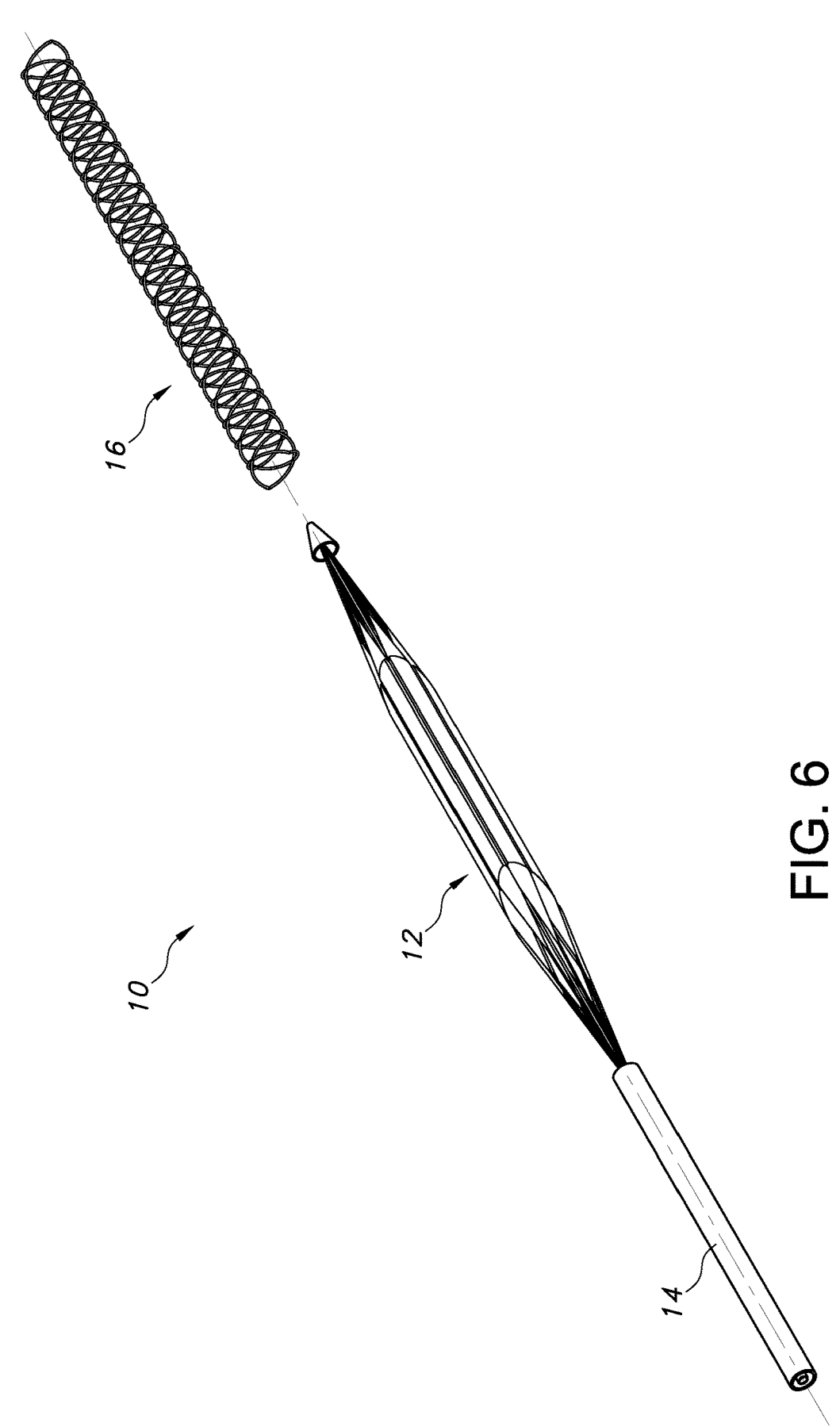
FIG. 6 is a perspective view showing an uninflated balloon being inserted into a flexible sock or sleeve.

The mesh 16 may be applied to the balloon 12 as a preformed sock, as indicated in FIG. 6, or may be applied to the balloon by winding a wire or wire-like material around the balloon 12 (possibly in a helical or spiral manner, as illustrated, in a single pass or double pass, and at a constant or variable pitch). All or portions of the mesh 16 may be connected to the balloon 12, such as by using an adhesive. The mesh 16 may be formed of woven wires or filaments, or non-woven wires or filaments, or may be cut from a piece of tubing (such as by forming openings in it). While the mesh 16 is shown as being arranged on the bias (that is, with wires or filaments that are angled or inclined), some of the filaments or wires may be substantially parallel to the central or longitudinal axis X, and others may be substantially perpendicular to it (such as would be the case if a screen-type material with regular, square openings were applied over the balloon 12, such as along the central portion B).

The mesh 16 may be a forming member configured to shape the balloon 12 in either (or both) the inflated or un-inflated states. In some variations, the mesh 16 may provide a compression force on the balloon 12. For example, the force of the mesh 16 may help compress the balloon from the expanded state shown in FIG. 4 into the unexpanded state shown in FIG. 3. Alternatively, a sheath (not shown) could be used to compress the mesh 16 after deflating the balloon 12.

Figure 2:
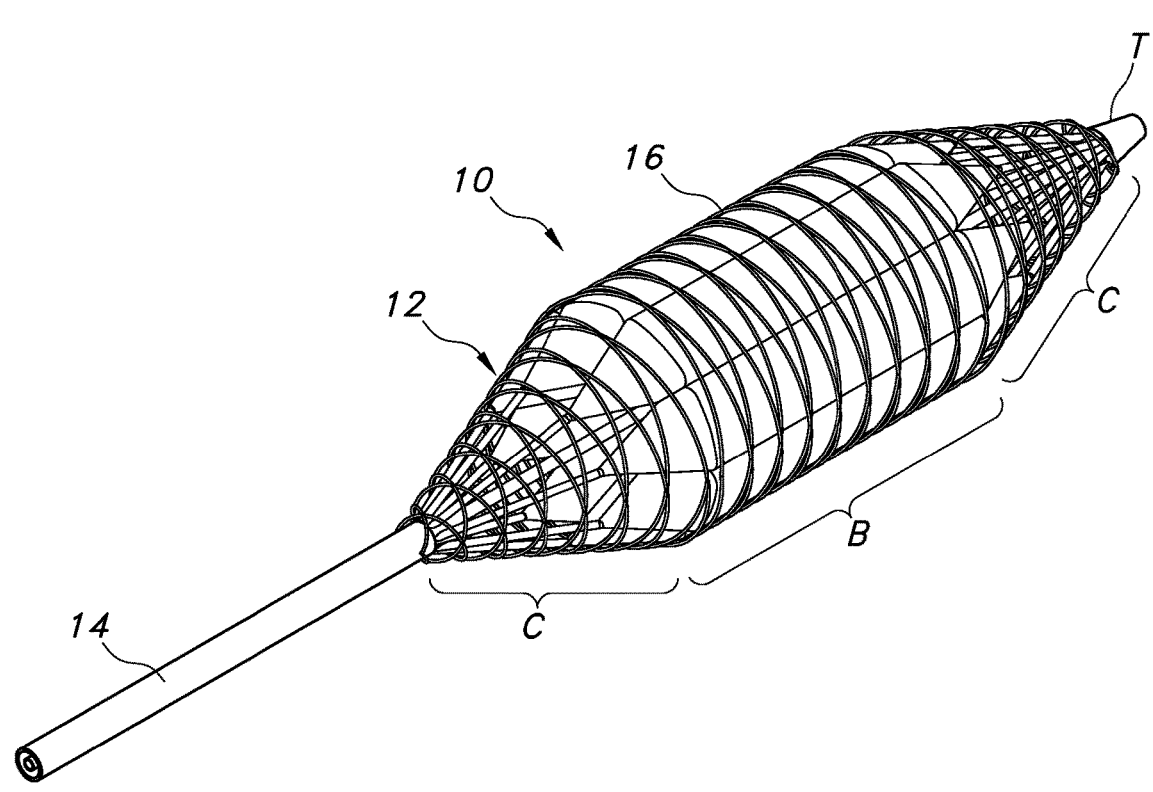
FIG. 2 is a perspective view of an inflatable device in the expanded condition including an outer mesh.
Figure 3:
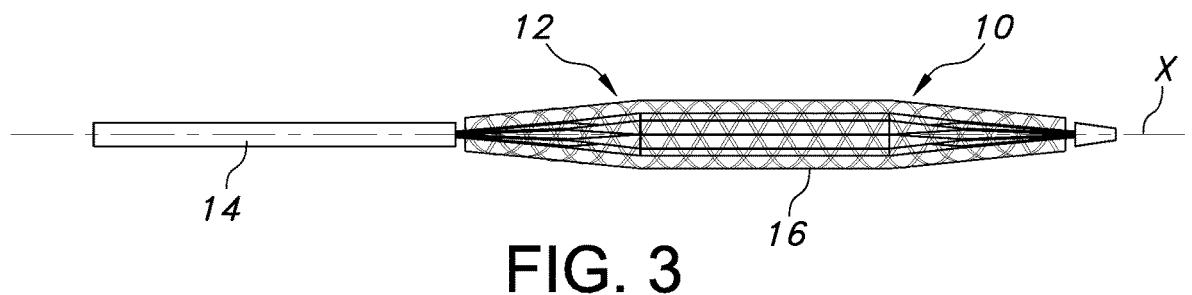
FIG. 3 is a side view of the device in an uninflated condition.
Figure 4:
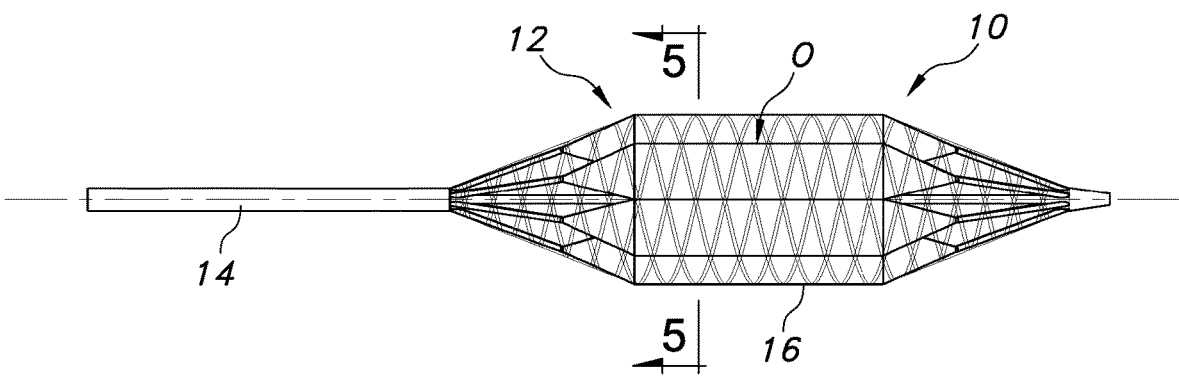
FIG. 4 is a side view of the device in an inflated condition.

The mesh 16 may extend along the entire balloon 12, as perhaps best understood from FIGS. 2, 3, and 4. Alternatively, the mesh 16 could extend over only a part of the balloon 12 (such as along all or part of the barrel portion B). The mesh 16 may also be provided in multiple portions or segments over all or part of the balloon 12 (that is, more than one piece of mesh may be used in connection with the balloon 12, including either in an overlapping or serial arrangement). A portion of the mesh 16 may also be provided with a gap or space with another portion of the mesh 16.

As can be appreciated, the mesh 16 includes a plurality of openings and, thus, forms a reticulated structure. The mesh 16 may be applied in a regular pattern, as shown, or may be irregular (such that, for example, wider openings are provided at some locations and smaller openings at others, including along the same or different portions of the balloon 12). The size and shape of the openings in the mesh 16 will depend on the manner in which it is formed.

Figure 5:
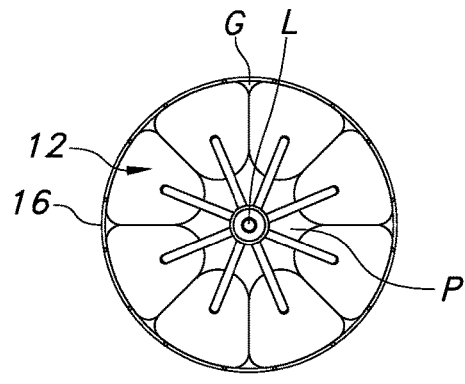
FIG. 5 is a cross-sectional view taken along line 5-5 of FIG. 4.

Regardless of the material used or form of it, the openings in the mesh 16 allow fluid to flow from an exterior region of the balloon 12 to an interior region, such as in the space or passage interior of the balloon inner surfaces juxtaposed with the central axis X. This not only includes flow from the proximal and distal ends of the balloon 12 if the mesh covers the tapered portions, but also along the central portion and within spaces between the cells 12a or balloons. In particular, the mesh 16 includes one or more openings O (see FIG. 4) positioned in juxtaposition or proximity to the gap between adjacent cells 12a that allows fluid to flow through any gap G or space formed between adjacent cells 12a (see FIG. 5), thus resulting in an enhanced level of perfusion and simplifying the construction without sacrificing the desirable features of a retainer (jacket or shell) for holding the cells together, both prior to and during inflation.

As can be appreciated, the disclosure also pertains to a method of forming a perfusion balloon. As noted above, the method may comprise providing a wire mesh over the perfusion balloon. This can be done by winding a wire over an outer surface of the balloon, or inserting the perfusion balloon into a tube formed of the wire mesh. The method may also include attaching the wire mesh to the perfusion balloon. The wire mesh may also be used to provide a compressive force on the balloon.

The foregoing discussion is intended to provide an illustration of the inventive concepts, and is not intended to limit the invention to any particular mode or form. Any elements described herein as singular can be pluralized (i.e., anything described as "one" can be more than one), and plural elements can be used individually. Characteristics disclosed of a single variation of an element, the device, the methods, or combinations thereof can be used or apply for other variations, for example, dimensions, burst pressures, shapes, materials, or combinations thereof. Any species element of a genus element can have the characteristics or elements of any other species element of that genus. Terms like "generally" or "substantially" mean that the value may vary depending on the circumstances, such as up to 10% of a given condition. The above-described configurations, elements or complete assemblies and methods and their elements for carrying out the invention, and variations of aspects of the invention can be combined and modified with each other in any combination, along with any obvious modifications.

The invention claimed is:

1. An apparatus for performing a medical procedure in the vasculature, comprising:

an inflatable perfusion balloon including a passage for transmitting fluid flowing through the vasculature in an inflated condition of the balloon; and a wire mesh positioned over at least a portion of the inflatable perfusion balloon;

wherein the balloon comprises a first cell and a second cell in a single cross-section of the balloon.

2. The apparatus of claim 1, wherein a space is provided between the first cell and the second cell, and openings in the wire mesh allow fluid to flow from external to the balloon, into the space, and to the passage.

3. The apparatus of claim 1, wherein the passage is surrounded by the first and second cells, and the wire mesh overlies the first and second cells of the balloon.

4. The apparatus of claim 1, wherein the first and second cells each include an inflation lumen.

5. The apparatus of claim 1, wherein the wire mesh comprises a metal.

6. The apparatus of claim 1, wherein the wire mesh comprises a shape-memory material.

7. The apparatus of claim 1, wherein the balloon comprises tapered end portions and a central portion, the wire mesh extending along at least the tapered end portions of the balloon.

8. The apparatus of claim 1, wherein the wire mesh comprises a reticulated structure including one or more openings in fluid communication with the passage when the balloon is inflated.

9. The apparatus of claim 1, wherein the balloon comprises a plurality of cells comprising the first cell and the second cell, each including a proximal neck for receiving an inflation fluid, and wherein the wire mesh at least partially covers the proximal necks of the cells.

10. The apparatus of claim 1, wherein the wire mesh comprises a helical wire.

11. The apparatus of claim 1, wherein the wire mesh includes holes that comprise a greater part of the area of the mesh than the solid material forming the mesh.

12. The apparatus of claim 1, wherein the mesh is woven.

* * * * *